United States Patent [19]

Kaster et al.

[11] 4,197,593
[45] Apr. 15, 1980

[54] ROTATABLY POSITIONABLE HEART VALVE AND METHOD

[75] Inventors: Robert L. Kaster, Wayzata; Donald N. Mehl, Minnetonka; Kathryn A. Klemetsrud, New Hope, all of Minn.

[73] Assignee: Kastec Corporation, Plymouth, Minn.

[21] Appl. No.: 882,972

[22] Filed: Mar. 3, 1978

[51] Int. Cl.² .............................................. A61F 1/22
[52] U.S. Cl. .............................................. 3/1.5; 3/1
[58] Field of Search ...................... 3/1.5, 1; 128/334 R

[56] References Cited

U.S. PATENT DOCUMENTS

| | | | |
|---|---|---|---|
| 3,623,212 | 11/1971 | Child | 3/1.5 |
| 3,691,567 | 9/1972 | Cromie | 3/1.5 |
| 3,763,548 | 10/1973 | Anderson | 3/1.5 X |
| 3,781,969 | 1/1974 | Anderson | 3/1.5 X |
| 3,800,403 | 4/1974 | Anderson et al. | 3/1.5 X |
| 3,825,957 | 7/1974 | Kaster | 3/1.5 |
| 3,959,827 | 6/1976 | Kaster | 3/1.5 |
| 3,996,623 | 12/1976 | Kaster | 3/1.5 |
| 4,017,911 | 4/1977 | Kafesjian et al. | 3/1.5 |
| 4,021,863 | 5/1977 | Woien | 3/1.5 |
| 4,079,470 | 3/1978 | Deeg et al. | 3/13 |

*Primary Examiner*—Ronald L. Frinks
*Attorney, Agent, or Firm*—Hugh D. Jaeger; Lew Schwartz; Joseph F. Breimayer

[57] ABSTRACT

An implantable heart valve including a suturing ring within which the body of the valve may be rotatably positioned following surgical implantation. The suturing ring is held to the valve body by binding means, such as an annular band or series of cord wraps. In one embodiment, the binding means may be heat-relaxed after the suturing ring has been bound to the valve body, thereby facilitating rotation of the valve body in the suturing ring. Slip ring means may be interposed between the suturing ring and the valve body to facilitate rotation. The slip ring means may be shaped to permit the binding means to hold the suturing ring tightly at its edges to the valve body to prevent the suturing ring from separating from the valve body at their mutually adjacent edges. The slip ring means may comprise a single ring or a pair of concentric slip rings having a mutual low-friction interface.

24 Claims, 4 Drawing Figures

U.S. Patent
Apr. 15, 1980
4,197,593
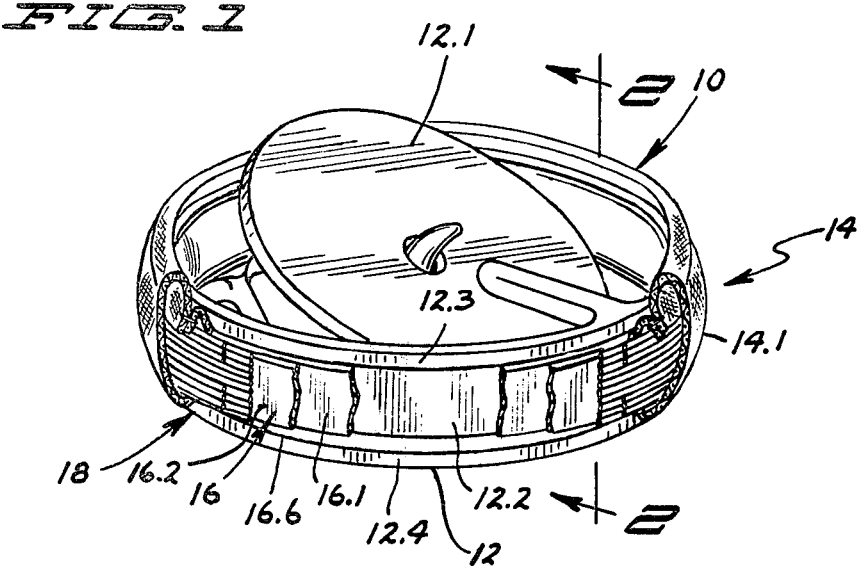
FIG. 1
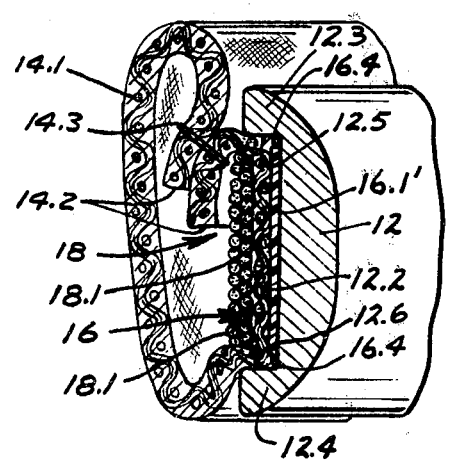
FIG. 2
FIG. 3
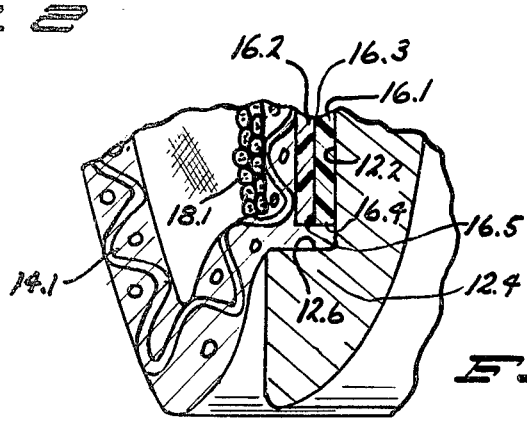
FIG. 4

ROTATABLY POSITIONABLE HEART VALVE AND METHOD

BACKGROUND OF THE INVENTION

Heart valves are commonly provided with a suturing or sewing ring which may be of fabric, the suturing ring being sewed by the surgeon to the peripheral tissue of a natural heart valve orifice after surgical removal of damaged or diseased natural valve structure. Following implantation, the surgeon may desire to adjust the valve by rotation of the valve body within the suturing ring so that the valving mechanism can properly operate without interference from surrounding heart tissue. Adjustment by rotation of the valve body should require a rotational force sufficiently small as to avoid damage to the sutured heart tissue or loosening of the sutures, and yet sufficiently great so that the valve, when properly positioned, does not further rotate when it is placed in operation. On the other hand, the suturing ring should be held tightly to the valve body so as to prevent the valve body and suturing ring from separating at their edges. Further, the method of manufacture of the valve should be such as to render the valve reliably rotatable within the ring within a narrow range of torque values; that is, the amount of torque needed to rotate the valve within the suturing ring should be substantially the same from one valve to another of the same size.

A number of methods have been proposed for retaining suturing members on heart valves, and certain of these methods have been summarized in U.S. Pat. No. 3,800,403. The last-mentioned patent describes a suturing ring which is provided with a heat-shrinkable annular plastic band. The valve body and surrounding suturing ring are heated to cause the band to shrink and to clamp the suturing ring onto the valve. The suturing ring itself is a torus-like element made of fabric, and the heat-shrinkable plastic band is positioned in the interior of the ring. Thus, during the shrinking operation, the band is hidden from view so that actual visual observation of the precise manner in which the heat-shrinkable band is clamped or positioned about the valve body is not possible. U.S. Pat. No. 3,623,212 disclosed a suturing ring which is held by means of threads or cords onto a valve body. Different ones of the threads, of course, exert different clamping pressures, and hence the clamping force across the width of the suturing ring may be uneven and the torque required to rotate the valve body within the ring is unpredictable.

It would be desirable to provide a heart valve body with a suturing ring in which attachment of the suturing ring to the valve body could be closely visually observed so as to detect and avoid any defects in material or errors in alignment of the components of the suturing ring on the valve body. It would further be desirable to provide such a valve which would permit the valve body to be rotated within the suturing ring upon application to the body torque within a narrow, predetermined range. It would further be desirable to so attach a suturing ring to a valve body as to substantially prevent the ring from being normally pulled even slightly away from the body.

SUMMARY OF THE INVENTION

The invention relates to a heart valve having a suturing ring within which the valve may be rotatably adjusted by a surgeon following suturing of the ring to a natural heart valve orifice. The valve includes a valve body having an exterior, annular wall, an annular suturing ring disposed about the wall, slip ring means positioned between the suturing ring and the wall and binding means positioned circumferentially of the wall and binding the suturing ring and slip ring means to the wall.

In one embodiment of the invention, at least one of the binding means and slip ring means are heat-relaxed after assembly of the suturing ring on the valve body to reduce the binding force of the annular binding means and to facilitate rotation of the valve body within the suturing ring. The binding means desirably comprises one or more tightly wrapped cords, heat relaxation of which tends to generally equalize the binding pressures of the cord wraps.

In another embodiment, the annular valve body wall has spaced, generally radially extending flanges defining between them an annular groove which desirably is generally flat-bottomed. The slip ring means consists of one or more slip rings disposed within the groove and having edges spaced from the flanges to define therebetween annular spaces for reception of edge portions of the suturing ring. The last-mentioned edge portions are held tightly within the annular spaces by the binding means to prevent the suturing ring from pulling loose at its edges from the valve body. In this embodiment, the torque required to initiate rotation of the valve body within the suturing ring may be adjusted by varying not only the binding force exerted by the binding means but also by varying the area of surface-to-surface frictional contact between the annular groove of the valve body and the slip ring or rings by making the latter wider or narrower.

In a further embodiment, the slip ring means includes at least one slip ring comprising a circularly formed strip of stiff, rigid material such as pyrolytic carbon. The thinness of the resulting ring provides a sufficient measure of flexibility to enable the ring to be readily assembled to the valve body. The ends of the strip, when the latter is in position about the valve body, may be spaced or may abut. If the ends are spaced, the torque required to rotate the valve body within the suturing ring will depend upon the binding force exerted by the binding means, the binding force urging the spaced ends of the strip toward one another. If the strip ends abut, the stress exerted by the strip against the valve body wall is substantially independent of the binding force exerted by the binding means, the rigidity of the strip preventing it from conforming more closely to the valve body.

In yet another embodiment, the slip ring means comprises a pair of slip rings having a mutual low-friction interface and disposed concentrically of the annular outer wall of the valve body. The slip rings are chosen such that when the valve body is rotated within the suturing ring, slippage preferentially occurs at the interface between the rings. The torque required to initiate rotation thus can be varied simply by varying the binding force provided by the binding means. Desirably, the binding means comprises a heat-relaxable annular element of polymeric material which may be a series of cord wraps or a continuous band, the binding force of which may be varied by controlled heating of the heat-relaxable material.

In the preferred embodiment, the slip ring means comprises a single ring of low friction polymeric material such as polytetrafluoroethylene ("Teflon TFE") and the binding means is provided by a series of cord wraps holding the suturing ring and slip ring to the exterior annular wall of the valve body. The cord is of heat-relaxable polymeric material, such as polyester, such that when the assembled valve is heated at temperatures of up to about 121° C., the secured cord wraps expand slightly under tension to reduce binding force, thereby facilitating rotation of the valve body. Relaxation in this manner further tends to equalize the binding force exerted by individual cord wraps. The slip ring desirably is of lesser width than the distance between flanges extending radially outwardly from edges of the circumferential valve body wall, and one or more cord wraps adjacent to the flanges press portions of the suturing ring into the resulting annular spaces between the slip ring edges and the confronting surfaces of the valve body.

The invention further relates to a method for providing prosthetic devices such as heart valves with suturing rings within which the devices may be rotatably positioned. Speaking broadly, the method involves binding a suturing ring to a prosthetic valve body with heat-relaxable binding means, and then heating the binding means sufficiently to at least partially relax the same and reduce the binding force exerted by it to facilitate rotation. The binding means preferably comprises an annular heat-relaxable polymeric element which may consist of one or more wraps of a polymeric sheet or cord. The method desirably includes the step of interposing slip ring means between the suturing ring and the valve body prior to the heat-relaxation step. Alternatively, the slip ring may be heat-deformable and may flow at least slightly away from relatively high binding force areas, thereby reducing the overall binding force.

DESCRIPTION OF THE DRAWING

FIG. 1 is a perspective view, partially broken away, of a rotatively positionable heart valve of the invention;

FIG. 2 is a cross-sectional view taken along line 2—2 of FIG. 1;

FIG. 3 is a cross-sectional view similar to that of FIG. 2, but showing a modification of the invention; and FIG. 4 is an enlarged cross-sectional view of the circled portion 4 of FIG. 1.

DETAILED DESCRIPTION

FIG. 1 depicts a heart valve 10 having an annular valve body 12 and an operating valve structure which includes a pivoting disc 12.1 and associated pivots and guides. The valve depicted in FIG. 1 is that of U.S. Pat. No. 4,021,863, the disclosure of which is incorporated herein by reference. It will be understood that the instant invention is not limited to any particular operating valve structure and indeed is applicable to ball-and-cage valves, floating disc valves, valves with multiple flaps or closures, and the like. All of these valves, however, are characterized by having an annular valve body carrying a circumferential suturing ring permitting the valve to be sutured to the orifice of a natural heart valve.

The annular valve body is desirably rigid, and may be made of titanium, stainless steel, pyrolytic carbon or the like. As depicted in the drawing, the valve body has an exterior, annular wall 12.2, the surface of which is desirably generally flat, but which may be concave or convex or of other configuration. Flanges 12.3, 12.4 extend generally radially outwardly from the valve body at or adjacent to the edges of the exterior wall 12.2. The confronting, generally parallel surfaces 12.5, 12.6 of the flanges are thus spaced apart a predetermined distance in the direction of flow, and these surfaces define between them, with the wall 12.2, an annular desirably generally flat-bottomed groove. As mentioned above, it may be desirable in some instances to make the bottom of the groove generally concave or convex, or the groove may have an irregular, wavy surface if desired.

A suturing ring is shown generally as 14 and comprises a strip of fabric made of synthetic fiber, such as polytetrafluoroethylene (e.g., "Teflon TFE") or polyester (e.g., "Dacron"). The fabric strip, designated 14.1, has longitudinal edges 14.2 which are sewn together to form a seam 14.3, the strip thus being formed into a torus-shaped ring. The suturing ring may be filled with a biologically acceptable spongy material, such as silicone rubber or polyurethane and the thus-filled ring may be formed and shaped as desired, one such shape being shown in the above-referenced U.S. Pat. No. 3,800,403. Desirably, however, the suturing ring remains unfilled, the fabric thereof being pulled sufficiently tight by the sewing operation as to retain a more or less rounded shape such as that shown in FIG. 1.

Slip ring means, shown generally as 16, includes one or more, desirably not more than two, generally flat polymeric rings. The embodiment shown in FIGS. 1 and 2 employs two such rings, of which one ring 16.1 bears against the annular wall 12.2 between the flanges 12.3, 12.4. The other ring 16.2 is concentric with and overlies the ring 16.1. The rings 16.1, 16.2 may be continuous; however, for ease of manufacture, it is desired that the rings be formed of narrow, flattened ribbons of polymeric material which can be manually laid about the wall 12.2 with the ends of each ring being closely adjacent one another or in actual abutting contact. The closely adjacent or abutting ends of the first ring 16.1 are in non-alignment with the ends of the first ring 16.2 so that the ends of the respective rings do not interfere with one another during rotation of the valve body within the suturing ring.

The slip rings 16.1, 16.2 are preferably of a slippery polymeric material such as fused polytetrafluoroethylene, but may be of other biologically compatible materials as well such as titanium foil, etc. As described, the slip rings 16.1, 16.2 have a mutual interface 16.3 having low-friction characteristics and permitting one ring to slip about the other ring with comparative ease. The longitudinal edges 16.4, 16.5 of the slip rings desirably are in radial alignment with one another and are spaced a small distance from the confronting surfaces 12.5, 12.6 of the valve body flanges so as to define narrow annular spaces between the adjacent portions of the flanges and slip rings.

Binding means 18 are shown in the drawing as a series of cord wraps 18.1. A single cord may be employed to make all of the wraps, or several wraps may be made with each of several cord lengths. The cords desirably are of a heat-relaxable material such as braided polyester ("Dacron"). The interstices of the braided cord may be filled with a polymer such as polytetrafluoroethylene. A particularly desirable cord is size 2-0 "Tevdek II", which is a polytetrafluoroethylene ("Teflon TFE")—impregnated, braided polyester ("Dacron") suture sold by the Deknatel Company.

Desirably, the binding means of the invention are "heat-relaxable". By this term is meant that the binding means, when heated to a preselected temperature in the range of from about 50° C. to about 140° C. (and preferably at temperatures of about 121° C.), relaxes and elongates slightly under the circumferential tension holding it to the valve body. The elongation of the binding material causes the binding force exerted by it to be diminished slightly, and the reduced binding force facilitates rotation of the valve body within the suturing ring. For example, the "Tevdek II" material referred to above, when placed under tension and heated for 25 minutes at a temperature of 121° C. increases in length. This material initially shrinks slightly when heat is first applied, but thereafter elongates as set out above. Repeated heating cycles do not appear to significantly further affect the length of the elongated material. The heat-relaxation of this material, it will be understood, tends to lessen differences in winding tension between different wraps of the material, thereby tending to equalize the binding force exerted by each wrap.

The binding means may also take the form of bands of polymeric material such as polytetrafluoroethylene and polypropylene, the material being manufactured by known processes to cause it to first shrink to exert binding force upon the suturing ring, and thereafter to heat-relax and elongating slightly, as set out above. In the preferred embodiment, however, a heat-relaxable polymeric cord is employed.

The embodiment of the invention shown in FIG. 3 is similar to that of FIG. 2 except that only a single slip ring 16.1' has been employed, the longitudinal edges 16.4 of the ring being spaced inwardly slightly from the confronting surfaces 12.5, 12.6 of the valve body to afford narrow annular spaces between the ring edges and the flanges. As in the embodiment of FIG. 2, the slip ring 16.1' desirably is formed of a length or strip of low friction material such as polytetrafluoroethylene, and is placed upon the valve body wall 12.2 so that the ends of the strip are closely adjacent or actually abut.

Assembly and Operation

Referring now to FIG. 2, the slip rings 16.1, 16.2 are first positioned correctly upon the exterior wall 12.2 of a valve body with the longitudinal edges of the rings being spaced from the confronting surfaces of the flanges and with the adjacent ends of one ring out of alignment with the ends of the other ring. For example, for a heart valve having an overall diameter of about 25 mm., the width of the groove defined by the confronting surfaces of the flanges and the wall 12.2 may be on the order of 3.44 mm., and the corresponding width of the slip rings may be approximately 3.14 mm. The material of the slip rings—preferably polytetrafluoroethylene—is desirably such that in thin sections (on the order of 0.127 mm.), the slip ring strips are relatively limp and easily conform to the annular wall 12.2. One or more of the slip rings as described may be made of a stiff, rigid material such as a sapphire or pyrolytic carbon (e.g., "Pyrolite", a product of General Atomic Company), or from a metal such as stainless steel or titanium. Preferably, only one such slip ring is employed, and comprises a circularly-shaped ribbon of material, the ends of which are spaced apart or abut. The thinness of the ribbon permits its ends to flex inwardly and outwardly slightly despite its stiffness to facilitate mounting the ring upon the value body. As mentioned previously, the edges of the ring are desirably spaced slightly from the confronting edges of the valve body flanges. The suturing ring 14, with its longitudinal edges not yet attached to one another, is then positioned about the exterior surfaces of the outer slip ring 16.2, care being taken to maintain the slip rings in their correct positions. The suturing ring material desirably is a continuous, unbroken circular band of fabric which may be provided with a central drawstring to draw the band snugly about the slip ring 16.2 and to hold the band in place during the subsequent application of the binding means.

The binding means, preferably in the form of cord, is then wrapped about the strip of suturing material to bind the same tightly to the valve body. Desirably, two or three wraps are taken with each length of cord. The cord is pulled tight to press the fabric to the slip ring, and the ends of the cord are then being firmly knotted together. The adjacent wraps extend across the width of the fabric overlying the slip rings. Care is taken to insure that the wraps extend into the proximity of the annular spaces between the edges of the slip rings and the respective confronting surfaces of the valve body flanges. The latter wraps serve to securely press the suturing ring fabric into the annular spaces, the fabric thus being forced firmly against the confronting surfaces 12.5, 12.6 of the flanges. Desirably, several additional wraps of cord overlying the annular spaces are taken, as shown in FIG. 2, to more firmly hold the suturing ring fabric in place and to prevent the same from being pulled away from the flanges.

The thus-assembled valve is then heated at a temperature of e.g., 121° C. for e.g., 10-45 minutes. The cord wraps 18.1, being under considerable circumferential tension, thus are permitted to heat-relax and elongate slightly. The valve is permitted to cool to room temperature, and the torque required to rotate the valve body within the suturing ring is measured with a small, sensitive torque wrench. Considerable force is required to initiate rotation after the heat-relaxation step. Thereafter, rotation of the valve may be re-initiated with considerably less applied torque. The magnitude of the latter torque (the torque required to re-initiate rotation) is measured and should fall within certain prescribed ranges. The range of acceptable torque values for small diameter valves (i.e., those adapted for implantation in small heart orifices) is generally less than the range of torque values for larger sized valves. For a heart valve having an external suturing ring diameter of 23 mm., for example, an acceptable range of torque values to re-initiate rotation would be from about 0.6 to about 0.8 Kg.—Cm.

The longitudinal edges of the strip suturing ring fabric are then brought together, as shown in FIG. 2, and stitches are taken about the periphery of the edges to form the seam 14.3.

Referring again to the embodiment shown in FIGS. 1 and 2, it has been found that rotation of the valve body within the suturing ring causes slippage at the interface between the two slip rings 16.1, 16.2. The inner slip ring 16.1 retains its position against the wall 12.2 of the valve body, whereas the outer slip ring 16.2 maintains its position with respect to the fabric suturing ring. The interface 16.3 between the slip rings has been termed a "low-friction" interface in that the coefficient of static friction at the interface between the slip rings is less than that at the interface between the inner ring 16.1 and the wall 12.2 of the valve body, and is also less than that at the interface between the suturing ring fabric and the outer ring 16.2.

The embodiment shown in FIG. 3 may be prepared in a fashion identical to that described above with reference to FIG. 2, except that but a single slip ring 16.1' is employed. Rotation of the valve body within the suturing ring produces slippage at the interface between the slip ring 16.1' and the wall 12.2 of the valve body. As between the embodiments of FIGS. 2 and 3, sizes and dimensions being equivalent, generally more torque is required to cause rotation of the valve body in the FIG. 3 embodiment. However, the FIG. 3 embodiment is preferred in that the torque values which are obtained tend to fall more closely within the desired ranges.

The rigid slip ring or rings described above, being slightly flexible because of its thinness, may be mounted to a valve body by gently spreading the ends of the ring and slipping the ring over one of the edge flanges of the valve body, the ring springing back into circumferential engagement with the wall 12.2. The ends of the ring may be formed to interlock with one another if desired to hold the ring in place.

Rotation of the valve body within the suturing ring not only leads to rotational slippage between the slip rings (FIG. 2) or between the slip ring and valve body (FIG. 3), but also requires slippage to occur between the fabric of the suturing ring and the valve body adjacent the flanges 12.3, 12.4. It will be understood that the torque required for rotation of the valve body within the suturing ring depends upon a number of variables in addition to the nature of the materials employed. For example, the coefficient of friction between the fabric of the suturing ring and the surface of the valve body is generally greater than that between the slip rings or between the slip ring and the valve body itself. Accordingly, the width of the slip ring or rings may be varied as desired, with the basic understanding that the torque required for rotation is increased as the width of the slip ring or rings is decreased. Further, the relaxation afforded the binding means depends upon the heating conditions to which the binding means is exposed, and some control can be exercised over the torque required for rotation by varying such heating conditions with the general understanding that more severe heating conditions will produce greater heat-relaxation of the binding means and will thus lead to a reduction in the torque required to rotate the valve body within the suturing ring. Of course the amount of heat-relaxation afforded the binding means is limited, and some friction forces will always be encountered when the valve body is rotated within the suturing ring.

Somewhat different effects are encountered when a rigid, stiff slip ring is employed. If the ends of the rigid ring are spaced slightly, then the pressure of the ring upon the valve body may be varied by varying the binding force exerted by the binding means. The inner surface of the rigid ring is desirably smooth so as to slide readily upon the smooth surface of the exterior wall of the valve body. However, if the ends of the rigid ring abut, then the rigidity and stiffness of the ring will largely restrain the ring from pressing more forcefully against the exterior valve body wall as the binding force is increased. In this manner, it is contemplated that the torque required for rotation may be even more closely controlled.

Prior to implantation of the valve, the valve body is rotated within the sewing ring to eliminate the initial resistance to rotation that may develop when the valve is stored over a period of time.

A convenient holder attached to the valve body is employed to properly position the valve in a heart valve orifice which has been prepared for the valve. The suturing ring is sutured by the surgeon to the natural tissue of the heart. The valve body may then be rotated within the suturing ring as desired by the surgeon so that the valve mechanism may operate without interference from surrounding tissue. During rotation, a counter rotation force is gently applied by the surgeon to the suturing ring to further reduce stresses on the sutured natural orifice tissue. As mentioned above, the torque required for rotation of the valve should be sufficiently small as to avoid rotational forces tending to loosen the sutures or damage the heart tissue which has been sutured to the suturing ring, but yet should be sufficiently high as to prevent the valve body from rotating within the suturing ring when heart function has been restored.

While we have described preferred embodiments of the present invention, it should be understood that various changes, adaptations, and modifications may be made therein without departing from the spirit of the invention and the scope of the appended claims.

What is claimed is:

1. An implantable heart valve having a valve body and an exterior suturing ring within which the valve body may be rotatably adjusted following suturing of the ring to a natural heart tissue orifice, the valve body having an exterior annular wall with the suturing ring disposed circumferentially of the wall, the valve including slip ring means interposed between the suturing ring and the wall and circumferential binding means binding the suturing ring and slip ring to the valve body wall, at least one of the binding means and slip ring means being heat-relaxed under controlled conditions to reduce the initial binding force of the binding means to thereby facilitate controlled rotational positioning of the valve body within the suturing ring.

2. The heart valve of claim 1 wherein the binding means comprises a plurality of circumferential wraps of a heat-relaxable polymeric cord.

3. The heart valve of claim 2 including spaced flanges extending generally radially from the annular wall of the valve body and defining with the annular wall an annular groove, the slip ring means having edges spaced from confronting surfaces of the flanges to define annular spaces, the cord wraps securely retaining circumferential portions of the suturing ring within the annular spaces.

4. The heart valve of claim 3 wherein the cord wraps are of a polymeric material capable of elongating under tension at a temperature in the range of about 50° C. to about 140° C., the material returning to a length greater than its original length upon cooling under tension to room temperature.

5. The heart valve of claim 4 wherein the slip ring means comprises a single ring of polytetrafluoroethylene.

6. The heart valve of claim 4 wherein the slip ring means comprises a pair of concentric slip rings having a mutual low-friction interface.

7. An implantable heart valve having a valve body and an exterior suturing ring within which the valve body may be rotatably adjusted following suturing of the ring to a natural heart tissue orifice, the valve body having an exterior annular wall and spaced, annular flanges extending generally radially outwardly of the wall to define with the latter an annular groove, slip ring means disposed within the groove and having peripheral edges respectively spaced from confronting flanges to define annular spaces at the edges of the slip ring means, a suturing ring carried circumferentially of the slip ring means, and binding means binding the suturing ring and slip ring to the valve body wall, the binding means including means securely retaining circumferential portions of the suturing ring within the annular spaces.

8. The heart valve of claim 7 wherein the binding means comprises a plurality of circumferential cord wraps, at least one cord wrap adjacent each valve body flange tightly retaining a circumferential portion of the suturing ring within the adjacent annular groove.

9. The heart valve of claim 7 wherein at least one of the binding means and the slip ring means is heat-relaxed to reduce the original binding force of the binding means and to thereby facilitate rotation of the valve body within the suturing ring.

10. The heart valve of claim 9 wherein the binding means comprises a polymeric cord wrapped to provide binding force binding the suturing ring and slip ring means and then heat-relaxed.

11. The heart valve of claim 9 wherein the slip ring means comprises a single flattened ring of polytetrafluoroethylene.

12. The heart valve of claim 9 wherein the slip ring means comprises a pair of concentric slip rings having a mutual low-friction interface.

13. The heart valve of claim 9 wherein the slip ring means comprises a rigid, stiff split ring having spaced ends.

14. The heart valve of claim 9 wherein the slip ring means comprises a rigid, stiff split ring with abutting ends.

15. A method for providing prosthetic devices such as heart valves with suturing rings within which the devices may be rotatably positioned, the method comprising binding a suturing ring to the prosthesis with heat-relaxable binding means, and controllably heating the binding means under predetermined conditions to at least partially relax the same and reduce the binding force exerted by it to facilitate rotation of the prosthesis.

16. The method of claim 15 including the step of interposing slip ring means between the suturing ring and the prosthesis prior to the heat-relaxation step.

17. An implantable heart valve having a valve body and an exterior suturing ring within which the valve body may be rotatably adjusted following suturing of the ring to a natural heart orifice, the valve body having an exterior annular wall, slip ring means circumferentially mounted about the annular wall of the valve body, the slip ring means comprising at least one stiff, rigid ring having abutting ends, a suturing ring carried circumferentially of the slip ring means, and binding means binding the suturing ring and slip ring to the valve body wall.

18. The heart valve of claim 17 in which the rigid, still slip ring is sapphire.

19. The heart valve of claim 17 in which the stiff, rigid slip ring is pyrolytic carbon.

20. The heart valve of claim 17 in which the stiff, rigid slip ring is of a material selected from the group consisting of stainless steel and titanium.

21. An implantable heart valve having a valve body and an exterior suturing ring within which the valve body may be rotatably adjusted following suturing of the ring to a natural heart orifice, the valve body having an exterior annular wall, slip ring means circumferentially mounted about the annular wall of the valve body, the slip ring means comprising at least one stiff, rigid ring having spaced ends, a suturing ring carried circumferentially of the slip ring means, and binding means binding the suturing ring and slip ring to the valve body wall.

22. The heart valve of claim 21 in which the stiff, rigid slip ring is sapphire.

23. The heart valve of claim 21 in which the stiff, rigid slip ring is pyrolytic carbon.

24. The heart valve of claim 21 in which the stiff, rigid slip ring is of a material selected from the group consisting of stainless steel and titanium.

* * * * *

UNITED STATES PATENT AND TRADEMARK OFFICE
CERTIFICATE OF CORRECTION

PATENT NO. : 4,197,593
DATED : April 15, 1980
INVENTOR(S) : Robert L. Kaster, Donald N. Mehl & Kathryn A. Klemetsrud It is certified that error appears in the above-identified patent and that said Letters Patent are hereby corrected as shown below:

Column 1,
 Line 58, after "body" insert --of--;

Column 3,
 Line 15, after "confronting" insert --flange--;

Column 5,
 Line 63, "value" should be --valve--;

Column 6,
 Line 48, after "strip" insert --of--;

Column 10,
 Line 16, "still" should be --stiff--.

Signed and Sealed this

First Day of July 1980

[SEAL]

Attest:

*Attesting Officer*

SIDNEY A. DIAMOND
*Commissioner of Patents and Trademarks*